United States Patent [19]
Milner et al.

[11] Patent Number: 5,595,746
[45] Date of Patent: Jan. 21, 1997

[54] INSECT PEST CONTROL

[75] Inventors: Richard J. Milner, Hall; Judith A. Staples, Bungendore; Michael Lenz, Ainslie; George G. Lutton, Fraser; Cheryl F. McRae, Campbell; John A. L. Watson, deceased, late of O'Connor, all of Australia, by Barbara D. Watson, legal representative

[73] Assignee: Commonwealth Scientific and Industrial Research Organization, Australian Capital Territory, Australia

[21] Appl. No.: 244,271
[22] PCT Filed: Nov. 23, 1992
[86] PCT No.: PCT/AU92/00629
§ 371 Date: Aug. 23, 1994
§ 102(e) Date: Aug. 23, 1994
[87] PCT Pub. No.: WO93/09672
PCT Pub. Date: May 27, 1993

[30] Foreign Application Priority Data
Nov. 22, 1991 [AU] Australia .................. PK9664

[51] Int. Cl.⁶ ........................................ A01N 25/02
[52] U.S. Cl. ............................. 424/405; 424/400
[58] Field of Search ..................... 424/405, 400

[56] References Cited

U.S. PATENT DOCUMENTS 5,057,315 10/1991 Gunner et al. .................. 424/93.1

OTHER PUBLICATIONS

Haemel, H., *Biological Abstracts*, vol. 73, 1982, #9273.
Haenel, H. *Biological Abstracts*, vol. 76, 1983, #79203.
Haenel et al., *Biological Abstracts*, vol. 76, 1983, #321,715.
Fernandes, P.M., *Biological Abstracts*, vol. 92, 1991, #499867.

*Primary Examiner*—Thurman K. Page
*Attorney, Agent, or Firm*—Sughrue, Mion, Zinn, Macpeak & Seas

[57] ABSTRACT

A method for selecting fungal species of strains metarhizium anisopliae suitable for control of a pest insect, species (termites) comprising applying conidia of a test fungal species of a strain to the cuticle of at least one target insect, introducing said at least one conidia-carrying target insect to a known number of uninfected target insects, and determining the proportion of dead target insects after a predetermined period.

22 Claims, No Drawings

5,595,746

INSECT PEST CONTROL

This invention relates to the use of fungus, particularly *Metarhizium anisopliae*, for control of termites and other pest insects. The invention provides methods for selection of suitable fungal species and strains, formulations and methods of culture and preparation.

Termite infestations have previously been controlled by the use of highly toxic chemicals such as arsenic and organochlorine based compounds. With the increase in awareness of the dangers of these chemicals it is now desirable to develop other effective means to control termites and other pest insects.

The fungus, *Metarhizium anisopliae*, is a known insect pathogenic fungus which infects a wide range of insects from many orders. The life cycle is simple: the asexual haploid conidia germinate on the cuticle of an insect sending out a germ tube which penetrates the cuticle and then buds off hyphal fragments into the haemolymph of the new host; these hyphal fragments grow and multiply eventually killing the insect; then, after death, the fungus grows through the cuticle of the insect and forms new conidia on the outside of the insect; and finally, the new conidia are passively dispersed.

The terms "spores" and "conidia" as used throughout the description and claims have the same meaning and as such may be read interchangeably.

*Metarhizium anisopliae* may be grown easily in vitro and will form copious conidia on standard mycological media such as Sabourauds's Dextrose Agar and natural substrates such as wheat, rice and barley. In liquid fermenters, the fungus may form mycelium which will sporulate either immediately or, if dries, after an interval of up to a year or more. Other methods of culture and preparation are reviewed below.

(i) In Brazil *Metarhizium anisopliae* is presently used on sugar cane for control of sap-feeding homopteran insects, particularly sugar cane froghopper (Mahanarva). The fungus is grown on moist boiled rice, allowed to sporulate, dried and milled into a powder. This powder may be stored under cool conditions and is generally mixed with water to form a suspension before spraying.

(ii) Bayer (Germany) have produced an experimental product (Bio-1020) including a strain of *Metarhizium anisopliae* as its active ingredient. This product consists of small granules of liquid fermenter-grown mycelium which, when applied to a moist substrate such as soil, sporulate within a few days to form conidia which in turn infect and kill the target pest.

(iii) Other workers have shown that strains of *Metarhizium anisopliae* when applied to termites as conidia will infect and kill the target termites. Furthermore, fungus mixed with talc and applied by dusting to nests or feeding sites of *Nasutitermes exitiosus* will cause substantial colony decline sometimes resulting in colony mortality. In particular, Hanel and Watson (Bull. ent. Res., 73, 305–313) found in field tests that the effect of *Metarhizium anisopliae* whilst useful for immediate use had a limited life span, and concluded that the factors inhibiting the completion of fungal development in the nest are unknown.

(iv) Kramm et al. [Journal of Invertebrate Pathology 40, 1–6 (1982)] observed that termites which have been exposed to whole cultures of *Metarhizium anisopliae* may transfer disease to previously healthy termites. It is suggested that this occurs by the healthy termites grooming live dosed termites. Importantly, however, it was noted that termites which have been killed by the fungus are avoided by healthy individuals.

In summary, whilst it is known that *Metarhizium anisopliae* has the ability to infect pests such as termites and subsequently infect previously healthy termites, the effective use of this fungus in the field has not been achieved. One reason for this is that it has been observed that healthy termites avoid infected termites which have died. However, *Metarhizium anisopliae* is highly variable genetically and individual strains differ substantially in their virulence for a particular host. These and a range of other difficulties with effectively using this technology in the field are apparent. Thus, whilst the fungus has previously been used in the laboratory to infect termites over a short period of time in a confined area, it has not been reported to be at all effective for use in the field.

It is an object of the present invention to overcome or alleviate at least one of the difficulties associated with effectively controlling termites in field applications by use of a fungus.

The first difficulty to overcome with developing an effective method for the control of termites in field application by use of a fungus is to provide a bioassay for the selection of fungal species and strains useful for the biocontrol of one or more termite species.

Accordingly, in one aspect, the present invention provides a method for selecting fungal species or strains suitable for control of termites, comprising applying conidia of a test fungal species or strain to the cuticle of at least one carrier termite, introducing said at least one carrier termite to a known number of uninfected termites, and determining the proportion of dead termites after a predetermined period.

Preferably, the test fungus is *Metarhizium anisopliae*. The selection of an effective isolate or strain of *Metarhizium anisopliae* depends on the following features: an isolate which will be pathogenic to the target under field conditions; is effective against several related species of target pest; and has a temperature profile which matches the prevailing field conditions. Initially it is important to assemble as large a library of isolates as possible. There are three main sources of isolates; culture collections, isolation from the environment of the target insect, and direct isolation from the target insect itself. *Metarhizium anisopliae* is easy to find in a wide range of habitats and the library of isolates which may be used in the present invention may be isolated from the environment of the target insect and/or directly from the insect itself.

The most obvious feature of *Metarhizium anisopliae* on isolation is the extreme diversity of colony types, viz. the colour of the conidia, the pattern of conidiation, the degree of sporulation, the colour and the texture of the aerial mycelium, the rate of growth, the level of pigmentation of the medium, and so on. It is possible to erect different morphological types and designate each isolate to a particular type. However, other characteristics (in particular pathogenicity) do not correlate with colony morphology and as the number of isolates to be so designated increases so does the difficulty of placing each isolate into a category.

The most powerful and reliable way to characterise isolates is by means of DNA analysis using modern polymerase chain reaction (PCR) technology.

In the bioassay the conidia may be applied to the carrier termite(s) cuticle by dusting or rolling the insect in dry conidia. The dose applied should generally be sufficient to permit the most efficacious fungal species or strains to kill approximately 50% of the termites in the bioassay within 10 days. Preferably the dose (expressed as the number of conidia on the carrier termite divided by the number of uninfected termites involved in the bioassy) may be in the range of $10^2$ to $10^5$, most preferably the dose is $10^3$ to $10^4$. Any number of uninfected termites may be used, but 25 to 1000 should provide meaningful results whilst remaining easy to count. The predetermined period, after which the proportion of dead termites may be determined, may be 1 to 14 days. Preferably, the predetermined period is 5 to 7 days.

It was found that all isolates were partially pathogenic. However, the preferred isolates were FI25, FI640, FI644, FI662, FI592, FI579, FI604, FI610, FI607, FI535 and FI726. In particular isolates FI610, FI726 and FI535 were the most preferred. The above isolates designations are those used by the Commonwealth Scientific and Industrial Research Organisatioon Pathogen Culture Collection.

Applicant found that these isolates were effective for control of a wide range of termite species in a variety of applications, in different geographic locations.

Another difficulty to overcome with developing an effective method for the control of termites in field applications by use of a fungus relates to the inherent difficulties of use of conidia.

The use of conidia as a biocontrol agent is complicated by a loss of conidia viability resulting from storage. There may also be problems due to dust generated during preparation. However, it has now been found, surprisingly, that these problems may be reduced by harvesting the conidia wet using a water plus wetting agent solution (e.g. Triton X-100). Furthermore, storage life may be improved by storing the conidia in a clay based formulation at a high moisture content.

Thus, in a second aspect, the invention provides a method of harvesting conidia comprising extracting the conidia from growth media in the presence of an aqueous solution of a water wetting agent.

Preferably the extraction comprises washing and settling in a dilute aqueous solution of a water wetting agent and is conducted under cool conditions (10°–30° C.). More preferably the extraction is conducted at about 20° C.

In a third aspect, the invention provides a method of storing conidia comprising formulating the conidia with clay to include a high moisture content.

Preferably, the conidia formulation is stored under cool conditions (10°–30° C.). The clay may be talc, attapulgite or mixtures thereof. The moisture content is preferably in the range of 20–35%.

Another difficulty to overcome with developing an effective method for the control of termites in field applications relates to the observed nature of healthy termites to avoid *Metarhizium anisopliae*. In some instances it has been observed that after a nest has been treated with a fungus that it has been possible for the treated portion of the nest to be sealed off by the termites and regular functioning of the colony to occur in the untreated portion of the nest.

Applicant has found that whilst there could be several mechanisms for this observation surprisingly it is the volatiles from the conidia which are thought to be an important component.

Accordingly, in a further aspect, the present invention provides a method of controlling termites in the field by use of *Metarhizium anisopliae* conidia or formulations thereof. This may be achieved by either one or a combination of the two following methods:

(a) A method of effectively controlling termites in the field which comprises treating an uninfested area or structure with a dose of *Metarhizium anisopliae* conidia or formulations thereof such that termites will avoid said area or structure;

(b) A method of effectively controlling termites in the field which comprises treating an infested area or structure with a dose of *Metarhizium anisopliae* conidia or formulations thereof such that the treatment will result in substantial colony mortality.

The term "area or structure" as used herein the description and claims includes but is not limited to the following: buildings, trees, gardens, earth and termite mounds.

In either method described above the *Metarhizium anisopliae* may be applied to the area or structure to be treated by any suitable means. The fungus may be prepared as a suspension or dust formulation or as a bait or granule.

Applicant has also found that conidia may be used effectively as pure dry conidia, or as a formulation. Thus, according to a further aspect of the invention there is provided an effective conidia formulation.

For treatment of an infested structure conidia may be formulated as a dust with either or both of the following: 1) an adsorbent to reduce repellency (e.g. activated charcoal), or 2) an attractant (e.g. powdered termite nest material, sawdust, cellulose, wood decayed by wood-decaying fungus, other attractant chemicals or mixtures thereof). The concentration of spores in this type of formulation is preferably in the range of from $5 \times 10^8$ to $10^{10}$ spores per gram.

For treatment as a repellent conidia may be formulated as:

1) dry pure conidia (e.g. mixed into soil, sand to provide a concentration of conidia of at least $10^8$ spores per g, more preferably $10^8$ to $10^9$ spores per g).

2) a dry powder formulation to be spread over a surface (e.g. dry conidia is attapulgite) to give an effective dose of preferably at least $10^8$ spores per $cm^2$, more preferably $10^8$ to $10^9$ spores per $cm^2$, 3) a concentrated suspension of conidia—to be watered onto a surface or to be painted or sprayed on to a surface to provide an effective dose of preferably at least $10^8$ spores per $cm^2$, more preferably $10^8$ to $10^9$ spores per $cm^2$.

Conidia may also be incorporated in a bait for either treatment of infested structures or as a repellent. Such baits may contain agar, andor other attractive and moisture-retentive materials as a base. The baits may also contain an attractant. The concentration of conidia in said baits is preferably at least $10^8$ spores per gram, more preferably $10^8$ to $10^9$ per gram.

In a particularly preferred embodiment pure conidia may be blown into a damaged (infested) structure. If *Metarhizium anisopliae* is to be used on an infected structure it is important to ensure that the appropriate amount of conidia is substantially distributed throughout the structure. This avoids the ability of healthy termites to sense the conidia and isolate the treated area and continue to cause damage in the untreated area. This may be preferably achieved by using pure undiluted conidia or a formulation of conidia and pumping it through the entire structure.

Any suitable pump or compressor may be used. One preferred type of portable system that may be used to pump a fungus is described in Australian Patent Application No. 8586191. Whilst the machine is designed to dispense arsenic tricocide dust, it has been used to dispense and distribute the fungus of the invention. The outlet of the machine is preferably attached via a (3 mm) plastic tubing to a copper tubing nozzle (internal diameter 2 mm) which is inserted into a termite "lead" (ie termite gallery or runaway), if available, or directly into cavities in the infested timber eg. architraves, skirting boards, door frames, floor boards, etc.

Sealing of the nozzle into the area to be treated is preferably achieved by use of plasticine or other molding clay around the nozzle, andor masking tape to seal off other apertures.

The machine is preferably run first on minimum (when spores are first added to bottle) and eventually on maximum as the bottle empties. Occasionally the bottle may be shaken to redistribute spores within bottle.

The bottle preferably holds approx. 5 grams spores (about two-thirds full), the bottle may be refilled approx. 4 times during a treatment in order to apply about 20 grams. Between 10 and 50 grams of spores per house are generally used for a single treatment, depending on the extent of damage and accessibility of timbers, and the size of the termite galleries.

Also, if damage and presence of live termite activity is extensive, damaged timbers may be treated at intervals along their length (e.g. every 1–2 meters.).

Treatment may also be repeated (i.e. more than one treatment per house) especially if termite activity is found at additional areas subsequent to the first treatment.

Pure spores, or a spore formulation may also be applied to a termite colony in a tree or mound by using a hand operated, double action push-pull pump. Preferably the pump is used at a pressure up to 5 $kgcm^2$ and a capacity of 5 liters per stroke (=300 liters per min. at 60 strokes).

A plastic specimen jar (preferred dimensions 45 mm diam.×75 mm height) containing up to 15 grams spores is preferably placed in the outlet line of the pump. The cap of the jar is preferably fitted with two plastic pipe joiners (internal diam. approx 3.5 mm, external diam. 4–8 mm) one of which acts as an inlet for air, and the other as the outlet for the spores. A vortex action is created by a continuous stream of air passing over the spores, so that a large quantity of spores (e.g. up to 30 g) can be rapidly blown into the termite colony.

The outlet from the jar is preferably connected to plastic tubing (preferred internal diam. 6 mm and approx. one meter in length), the distal end of which is plugged, and several holes have been made in preferably the last 25 cm of the tubing so that spores can be dispensed in a number of different directions.

To treat a mound colony, at least one hole is drilled by hand towards the centre of the mound using a wood auger (about 20 mm diameter) until the softer central nursery area (in the case of *Nasutitermes exitious* especially) is detected. The plastic tubing with holes is then inserted into the drill hole and the spores pumped in. The drill hole is then covered with a rock or branch (to prevent entry of marauding ants).

To treat a tree colony a very similar procedure is undertaken and would be apparent to the addressee. Ideally the nest is located and the tubing is inserted into the tree towards the centre of the nest.

If *Metarhizium anisopliae* is to be used as a repellent then it may be applied to the area termites are to be repelled from by any suitable means. Preferably conidia formulations of the fungus may be directly applied to soil or uninfested structures. In one embodiment where a structure such as a house is to be protected from termite infestation, a conidia formulation may be applied to an area of soil circumventing the structure.

Alternatively, or in addition, conidia or conidia formulation may be sprayed under a suspended floor andor sprayed onto vertical surfaces. To be effective over a long period of time the vertical surfaces are protected from UV radiation and high temperature.

Although described in relation to termite control, it should be understood that the methods of harvesting and storing according to the present invention may also be suitable for control of other pest insects. The invention will now be described with reference to the following non-limiting examples.

EXAMPLE 1—SELECTION OF STRAINS FOR TERMITE CONTROL

Strains of *Metarhizium anisopliae* may be isolated from termites, termite contaminated material such as feeding sites, or termite nest material. Strains were isolated from termite nest material as follows:

Termite nest material was crumbled or ground with a mortar and pestle. Approximately 1 g of each sample was transferred to 100 ml plastic srew-capped container to which 0.05% Tween 80 solution (approximately 100 ml) was added and sonicated. The nest material was then resuspended by invertinggently shaking the container. Using either plastic (disposable) or wire (alcohol flamed) loops, approximately 10 μl of each resuspended sample was spread over separate Veen's agar plates and the plates incubated in vented plastic bags at 25°–28° C., for two weeks. (Veen's agar: per liter 35 g mycological agar (Difco), 1 g chloramphenicol, 0.5 g cycloheximide. Add 1 liter distilled water, stir, cover. Autoclave for 10–15 minutes at 18 $lbin^2$. Cool to approx. 52 C., pour plates in laminar flow cabinet). The plates were then examined for green to yellowbrown colonies with bullet-shaped conidia (checked using phase contrast microscope at 400×). Finally, all colonies were individually sub-cultured on Sabourauds Dextrose Yeast Extract Agar.

Isolates were stored under ultralow temperature conditions (−70° C. to −196 C.) as dry conidia to preserve viability and ensure genetic stability.

To select those strains best suited for biocontrol of termites, each isolate strain was subjected to the following bioassay.

The conidia of the particular strain are grown on agar medium and are removed from the culture by scraping; then a worker termite is rolled in the dry conidia so that the conidia remain on the cuticle. The carrier termite is then added to a group of uninfected termites (usually 50) under conditions of 100% relative humidity and 28° C. The uninfected termites groom the carrier termite thereby distributing the conidia around the group. The bioassay is assessed by determining the proportion of the termites which die in a specified time period (usually up to 10 days). The dose may be varied by using dry talc to dilute the conidia dust used to treat the carrier termite. The number of conidia used may be determined by counting using a haemocytometer or by means of a viable colony count.

From a library of over 100 isolates tested, using this bioassay, some 9 isolates have been found to possess high virulence for both Nasutitermes and Coptotermes app. The dose (expressed as the number of conidia on the carrier termite divided by the number of uninfected termites added to the bioassay chamber) required to kill 50% of the termites was approximately $10^3$ to $10^4$.

In a further method to determine the best strain, a colony of termites (about 25 g) was established in a jar and provided with moist nest material as substrate and wood as food. Two hundred and fifty carrier termites treated with pure conidia of the appropriate isolate, were then added to the colony to give a ratio of about 1:50, carrier to test termites. The colony was then maintained at 26° C.–28° C. for one to four weeks. The efficacy of the strain was determined by the number of termites killed and the visible production of new conidia on the killed termites.

RESULTS: for *Coptotermes acinaciformis*

After four weeks incubation at 26° C.–28° C.

| Isolate | % kill, reps | | | Average |
|---|---|---|---|---|
| | 1 | 2 | 3 | |
| FI 25 | 95.5 | 100 | 100 | 98.5 |
| FI 640 | 56.7 | 34.1 | 60.6 | 50.5 |
| FI 644 | 62.3 | 60.3 | 85.7 | 69.4 |
| FI 662 | 50.3 | 73.6 | 90.6 | 71.5 |
| FI 592 | 52.3 | 60.0 | 50.8 | 54.3 |
| FI 579 | 88.8 | 100 | 100 | 96.3 |
| FI 604 | 70.6 | 60.2 | 98.0 | 76.3 |
| FI 610 | 100 | 100 | 100 | 100 |
| FI 607 | 100 | 54.9 | 47.0 | 67.3 |

EXAMPLE 2

This example shows that there are a range of isolates of *Metarhizium anisopliae* which are highly pathogenic for termites.

MATERIALS AND METHODS 1. 17 isolates known to be genetically distinct from DNA studies were grown on Sabourauds Dextrose Agar with 1% yeast extract.

2. The isolates were tested for their pathogenicity to worker termites (*Nasutitermes exitiosus*) by dipping into suspension of either $10^7$ or $10^5$ conidia/ml. The dosed termites were placed 10 per well in a 12-well microtitre tray and incubated in a constant temperature room at 26°–28° C. There were 120 termites dosed at each concentration for each isolate and a similar number of controls.

3. After 4 days the number of termites dead in each treatment was assessed.

RESULTS

| Isolate | % mortality ($10^7$ conidia/ml) | % mortality ($10^5$ conidia/ml) |
|---|---|---|
| FI123 | 100 | 20.8 |
| FI125 | 99.6 | 22.1 |
| FI147 | 82.9 | 17.5 |
| FI198 | 100 | 28.3 |
| FI389 | 54.3 | 11.4 |
| FI401 | 93.3 | 22.1 |
| FI522 | 100 | 15.0 |
| FI527 | 95.0 | 19.6 |
| FI535 | 100 | 35.0 |
| FI550 | 100 | 30.4 |
| FI592 | 100 | 26.7 |
| FI610 | 100 | 45.0 |
| FI628 | 100 | 15.2 |
| FI698 | 5.0 | 10.0 |
| FI702 | 9.9 | 16.7 |
| FI726 | 100 | 47.2 |
| Control | 17.5 | 17.5 |

These results indicate that several isolates are effective for termite control, especially FI610, FI535 and FI726.

EXAMPLE 3—PRODUCTION AND FORMULATION OF CONIDIA

The selected strains can be grown on a range of natural substrates under solid and liquid fermentation conditions. For example rice (800 g with water added to a total volume of 1600 ml) was steamed within an aerated aluminium tray (500×365×100 mm) and inoculated by spraying using a pressurized air paint sprayer with 15 ml of a $10^8$ conidia/ml suspension of the selected strain under aseptic conditions. The tray was then covered and incubated at 23° C. for about 2 to 3 weeks. The rice become covered in new green conidia of the Metarhizium strain. About $5 \times 10^9$ conidia were produced per gram dry weight of rice (i.e. one tray containing 800 g of rice produced about $4 \times 10^{12}$ conidia). The conidia were then harvested from this rice using a special extraction apparatus developed by Sutherst et al. (1987 Bull. Ent. Res. 77, 239–246) using a 0.05% aqueous solution of Triton X-100 under cool conditions (about 20° C.). Finally, the conidia were collected as either a suspension, or as a powder by using a clay such as talc or attapulgite to coagulate the fungal conidia and then filtering the water off the clayconidia mixture using a paper filter.

The collected conidia may be formulated in a number of manners:

1. As a liquid using additives to minimize settling of the conidia and to protect the conidia during storage.

2. As a dust in an inert substrate such as talc or attapulgite.

3. As a granule using material such as gelatine, plaster of Paris or alginate as a binding agent.

The fungus may be stored either formulated or unformulated. Under optimal conditions the conidia can be stored for over 12 months at 25° C. To ensure this length of storage the conidia must be washed from the rice substrate to ensure clean pure conidia, must be kept moist and cool during harvesting and formulation, and formulated into attapulgite at 20–35% moisture and a concentration of at least $5 \times 10^9$ per gram. It is important that this moisture be maintained during storage.

EXAMPLE 4

The fungus may alternatively be inoculated onto 150 mm diameter Petri plates containing Sabouraud's Dextrose Agar with 1% yeast extract (SDAYE agar). The plates are incubated at 25° C. for 3–4 weeks, after which the plates are inverted and the spores can be tapped off (or lightly scraped off). the spores are sieved through approximately 1 mm mesh to break up clumps and to help remove excess moisture. The spores can then be stored in plastic specimen containers of about 80 ml capacity, filled to no more than about two thirds full, and with the lid left slightly loose (to allow oxygenation), at 4° C. for several months. (Spores can also be stored pure at −70° C. for much longer periods or in cryoprotectants such as glycerol.)

The conidia, or spores, can be used pure as a dust to be blown in to termite nest mounds or tree nests or infested house timbers, as described elsewhere.

Alternatively, the conidia can be formulated with other powders such as talc, attapulgite etc., or can be formulated as an aqueous suspension for spraying, watering or painting.

The pure conidia can also be incorporated into baits, either dry or wet, such as agar-based formulations also containing wood or other attractant materials for termites.

EXAMPLE 5—USE IN TERMITE PEST CONTROL

The fungus may be used in several ways to control termites:

1. A concentrated suspension or dust formulation (at least $10^9$ conidia per ml or per g) may be used to treat feeding sites of termites such that the feeding termites are given as large a dose of conidia as possible. These termites will return to the colony, be groomed by other termites, and may die. It is thought that termites may be infected from one or more of the following sources; the initial inoculum, grooming or sporulating cadavers.

2. Mound-nests of termites may be killed by application of the fungus in a liquid or a dust formulation to the inside of the nest (at a dose of at least $3\times10^{10}$ spores per nest). A hole (or holes) are made in the nest wall into the nursery area and the fungus material blown into the nest such that maximal distribution in the galleries of the nursery and other parts of the nest are achieved.

3. Baits of granules (containing at least $10^8$ conidia per g) may be used to treat termites in soil and around structures to be protected, so that the termites become contaminated with conidia and thus again provide a source of inoculum to kill other termites in the colony.

EXAMPLE 6

This laboratory experiment shows that termites are repelled by conidia or *Metarhizium anisopliae* strain FI610.

RESULTS

1. The basic apparatus consisted of a 14 cm diameter plastic Petri dish marked on the base with a grid. The base of the Petri dish was covered with water agar and a 5 cm plug of agar placed in one corner. A 2 g "bait" of moist mound material was placed on the centre of this plug. In the treated dishes, the surface of this plug was covered with conidia of FI610 (about $3\times10^8$ per plug) and then the "bait" placed in top of the conidia. In the control dishes this surround was not treated.

2. Twenty *Coptotermes lacteus* soldiers were placed in each of 3 replicates of the controls and treated dishes. The plug was covered with an upturned pill box for the 30 minutes after the soldiers were added as a settling in period. The dishes were incubated in a constant temperature room at 26°–28° C.

3. The dishes were observed over three 5 minute periods each hour for 8 hours (except for the sixth hour when no reading was possible) after the settling in period. The number of termites on the plug was recorded and expressed as an average for each hour.

RESULTS

| Time (hr) | 1 | 2 | 3 | 4 | 5 | 7 | 8 |
|---|---|---|---|---|---|---|---|
| Treated | 0.1 | 0.1 | 0.3 | 0.3 | 0.3 | 0.2 | 0.2 |
| Control | 4.2 | 3.2 | 9.3 | 9.4 | 9.0 | 11.0 | 10.5 |

CONCLUSION

These results show that the conidia of FI610 repelled the termites and thus they were not able to reach the mound material which is normally attractive.

EXAMPLE 7

This example shows the efficacy, under simulated field conditions in the laboratory, of *Metarhizium anisopliae* FI610 as a soil treatment to prevent termites damaging timber.

MATERIALS AND METHODS

1. The basic apparatus consisted of a plastic lunch box (22 cm×13 cm×9 cm) with a 1.5 cm hole in one side to which an 8 cm×9 cm jar termite-colony could be attached such that the termites could forage in the lunch box. The jar contained 15 g of termites together with moist mound material but no food. The termite colony in the jar was allowed to settle for some weeks before being placed in the experiment.

2. Each lunch box was filled with 1.5 Kg of potting mix and firmly packed down. In the treated boxes half the soil surface (the half furthest from the termite colony) was treated by being evenly spread with 5 g of a mixture of FI610 conidia and talc. The concentration of this mixture was $1.5\times10^{10}$ conidia g. A block of *Eucalyptus regnans* wood (5 cm×5 cm×2 cm) was inserted horizontally in the treated half of the lunch box.

3. 4 lunch boxes were set up with *Nasutitermes exitiosus* and 4 with *Coptotermes acinaciformis*. There were 2 untreated control boxes for each species. The boxes were incubated in the dark at a constant temperature room running at 26°–28° C.

4. The damage to the wood block was assessed after 3, 6 and 12 months. Severely damaged blocks were replaced. After 12 months all boxes were destructively sampled and the termites checked.

RESULTS

After 3 months all the control blocks were severely damaged and replaced. There was no evidence that termites had penetrated the treated soil to reach the blocks in the treated boxes of either species.

After 6 months the results were again the same except for a single replicate of *C. acinaciformis*. In this replicate the termites had built a gallery across the lid of the treated box and attached the wood block from above. Observations suggested that the termites were dead in the treated and possibly control boxes by this time.

After 12 months, the termites were examined and found to be infected by Metarhizium in the treated boxes but not in the controls. However, all termites were by then dead.

CONCLUSIONS

These results show that surface treatment with Metarhizium FI610 conidia can prevent damage to susceptible timber under these laboratory conditions. The termites did not seem to enter the potting mix on the treated side even though the conidia were only on the surface.

EXAMPLE 8

This example shows the efficacy of *Metarhizium anisopliae* (strain FI610) conidia for protection of susceptible timber from attack in the field.

METHODS AND MATERIALS

1. A site was chosen near to active colonies of *Coptotermes frenchi*.

2. The soil was removed from 16 plots each measuring 30×30 cm and 10 cm deep. For the controls the soil was replaced untreated and a single block of susceptible timber placed vertically in the centre so that the top of the timber was flush with the soil surface. Half the plots were then "covered" with a cement slab measuring 30 cm×30 cm while the other half were left "exposed".

3. Conidia of the FI610 strain of the fungus grown on rice was used for the treatments. One plot of each treatment was covered and the other plot exposed. The following treatments were used:

(a) *Pinus radiata* wood blocks (5 cm×5 cm×22.5 cm) dipped into a concentrated suspension of conidia (about $10^{10}$ spores per ml) and left to dry before being inserted vertically into the soil.

(b) the surface of the soil was treated with conidia in attapulgite to give a final dose of $6\times10^7$ conidia per $cm^2$; a block of *P. radiata* 20 cm×20 cm×12 cm was then placed horizontally on the soil surface (=test block) and in addition, a single *P. radiata* wood block was inserted vertically to act as a "feeder strip" towards the test block.

(c) the surface of the soil was watered with an aqueous suspension of conidia so that the final dose was $8\times10^7$ conidia per $cm^2$; a test block of *P. radiata* was placed on the surface, and a feeder strip was also included, as in (b).

(d) the soil was mixed with dry conidia to give a final dose of $10^8$ conidia per g soil and the soil replaced into the ground; a single *P. radiata* wood block was inserted vertically as a test block.

(e) all treatments were applied and were replicated 6 times.

(f) after 24 weeks the blocks were removed and examined for termite damage. They were rated as either damaged (some slight surface damage but no penetration of the wood by the termites) or damaged (usually largely destroyed by termites). Also a sample of soil (where appropriate) was taken back to the laboratory and the number of conidia of the fungus still able to grow on a selective medium determined.

RESULTS

The results after 24 weeks were:

| Treatment | Covered or Exp. | No. Blocks | No. Damaged | % Conidia Survival |
| --- | --- | --- | --- | --- |
| a | C | 6 | 3 | nd |
| a | E | 6 | 1 | nd |
| b | C | 6 | 0 | 62 |
| b | E | 6 | 0 | 3 |
| c | C | 6 | 5 | 28 |
| c | U | 6 | 4 | 0.6 |
| d | C | 6 | 2 | 55 |
| d | U | 6 | 2 | 73 |
| control | | | | |
| (surface) | C | 12 | 10 | na |
| (surface) | E | 12 | 11 | na |
| control | C | 12 | 12 | na |
| | E | 12 | 11 | na | nd = not determined
na = not applicable
C = covered
E = exposed

CONCLUSION

In all cases treatment with Metarhizium was able to prevent damage due to termites. In particular the surface treatments with dry conidia in attapulgite and the mixing of dry conidia with soil were very effective. While it is possible that the fungus was protecting the wood by means of killing termites this is unlikely given that several days are needed for the fungus to kill. It is most likely that the fungus is acting to repel the termites. Chemical pesticides are tested in this manner and at least some are deemed to act by repellency rather than killing.

EXAMPLE 9

This example shows that termites (*Coptotermes acinaciformis*) from a nest just outside a house were controlled by treatment with a dust of FI610 conidia.

1. The house problem was referred to us by a pest controller. On inspection a nest of *C. acinaciformis* was found in a sleeper retaining wall just outside the house. Previous damage in the house was not seen as it had been repaired.

2. Sixteen grams of conidia of FI610 (about $5\times10^{11}$ conidia), produced on rice, were shaken by hand over the top of the sleepers and in towards the nest.

3. The sleeper wall was taken apart 4 months later and the nest was found to be dead with no king or queen and only a few bring remnant soldiers and workers nearby. A further 5 g of FI610 conidia were dusted onto the remaining termites that day.

4. No reports of further problems or damage have been reported and the initial treatment was conducted over 16 months ago.

EXAMPLE 10

This example shows the efficacy of dry conidia treatment of a house where the termites were still actively damaging.

1. The house was referred to us privately and was in the country in N.S.W. Termite activity and damage was evident on inspection. Damage was to skirting boards, and adjacent stairways. The termites were identified as *Coptotermes frenchi*. This house, built in 197576, had been perimeter treated with chlordane in 1987. Inspection of the skirting boards two years prior to our inspection did not reveal any termite problem.

2. After inspection 20 g of pure conidia of FI610, produced an agar, were blown into the damaged areas of wood and at intervals of about 1 m along the skirting board around the room using a compressor. The holes were sealed with tape.

3. two and a half months later the treated timber in the house was opened and no termites were found. Trees examined around the house were found to contain termites feeding on inserted dowelling bait. One of these trees could have contained a nest but was not treated at that time.

4. Two weeks later a sample of living *Coptoterme frenchi* was taken from a woodpile close to the house. On incubation in the laboratory it was found that 40% of these termites were infected with Metarhizium.

5. Approximately 3 months after the initial treatment the owner reported damage to the mezzanine area above the treated area, however inspection revealed this to be old damage and few live termites were seen. Nevertheless another 15 g of FI610 was blown into the area using a compressor.

6. Approximately 4 months after the initial treatment the house was again inspected and found to be free of termites as was the woodpile. However, a live termite sample was taken from a nearby cut tree stump. On incubation in the laboratory 100% of these termites died of Metarhizium.

7. Approximately 10 months after the initial treatment trees near the house were again drilled and inspected and no termite problems were found. However 15 g of dry conidia of FI610 were blown into two living trees where termite feeding previously was apparent (to keep owner happy).

CONCLUSION

It is expected that the original treatment was all that was necessary to control the termites in this house. However the owner was worried every time a termite was found and therefore subsidiary treatments were applied. The termites appear to have been controlled though the whereabouts of the nest was not confirmed.

EXAMPLE 11

This experiment shows that conidia of FI610 blown into a mound of *Coptotermes acinaciformis* in the field in the Darwin area can destroy the colony.

MATERIALS AND METHODS

1. Thirty-six mounds of *Coptotermes acinaciformis* were selected at a site near Darwin.

2. Nine mounds were left untreated as controls and the other mounds drilled with a 1.5 cm hole from the side to the base. Then pure conidia of FI610 grown on plates of Sabourauds Dextrose agar with 1% yeast extract were blown in using a two way action hand pump. Six mounds each were treated with 1 g, 5 g, 10 g, 20 g and 30 g of conidia. The mounds were treated on 18 May 1992.

3. All mounds were destructively sampled on 11 Aug. 1992, except for 2 mounds at 5 g and 3 mounds at 1 g. This was because other mounds at these lower treatment doses took longer to die and consequently the treatments were allowed to continue for sampling in November, 1992.

4. Mounds were rated as healthy—large numbers of workers, soldiers, nymphs as well as queens: dying—queen killed and few termites left with no nymphs, or: dead—only a few remnant workers termites left alive.

5. A sample of 25 living workers were taken from 1–3 replicate mounds and returned to the laboratory to determine whether or not they were infected with Metarhizium.

RESULTS

| Dose Infection | No. Mounds Healthy | No. Mounds Dying or Dead | % |
| --- | --- | --- | --- |
| Control | 8 | 1 | 0 |
| 1 g | 0 | 3 | 59.3 |
| 5 g | 0 | 3 | 79.0 |
| 10 g | 0 | 6 | 72.0 |
| 20 g | 0 | 6 | 78.0 |
| 30 g | 0 | 6 | None Living |

CONCLUSION

Similar results have been observed for another isolate FI535 in respect of *Coptotermes acinaciformis* also in the Darwin area. Further, FI610 has also been found to be effective for control of *Nasutitermes exitiosus* near Canberra.

These results indicate that conidia of FI535 blown into mounds of various species of termites are very effective in controlling the termites under these field conditions.

EXAMPLE 12

This describes an experiment where termites (*Neotermes rainbowi*) nesting in the trunks of palm trees were successfully controlled by blowing a mixture of conidia of FI535 and talc.

MATERIALS AND METHODS

1. Coconut palm trees or stumps showing visible external signs of termite invasion were selected and holes drilled (1.6 cm diameter) to the more central parts of the area occupied by the colony. A piece of clear plastic pipe (1.2 cm diameter) was inserted into the hole and the surrounding cracks sealed with "Blue-tac". Other holes were also sealed.

2. The fungal inoculum formulated as a 1:1 mixture of conidia and talc was blown in through this plastic pipe at doses of 5, 10, 12 or 15 g formulated material per tree.

3. The stumps were dissected with a chain saw 2 weeks after treatment and the effect on the number and health of the termites was assessed visibly as successful (no living termites), partially successful (a few live termites still present) or failure (no apparent effect).

RESULTS

| No. g Formulation | No. Stumps Treated | No. Successful | No. Partial Success | No. Failure |
| --- | --- | --- | --- | --- |
| 5 | 2 | 1 | 0 | 1 |
| 10 | 1 | 0 | 1 | 0 |
| 12 | 1 | 1 | 0 | 0 |
| 15 | 8 | 5 | 2 | 1 |

In all cases which failed this was due to not applying the fungus to the centre of the colony.

CONCLUSIONS

Blowing conidia of FI535 into a colony of *Neotermes rainbowi* was effective in controlling the colony even at doses as low as 5 g if the application was made directly into the nest.

Other aspects of the present invention, and modifications and variations thereto, will become apparent to those skilled in the art on reading this specification, and all such other aspects and modifications and variations are to be considered as included within the scope of the present invention.

We claim:

1. A method of controlling termites in field applications comprising applying to an uninfested, termite-infestable structure, a prophylactic effective dose of conidia of a strain of *Metarhizium anisopliae* or formulations thereof, such that said structure will not suffer damage from termites.

2. The method according to claim 1, wherein the strain of *Metarhizium anisopliae* is selected from the group consisting of isolate FI610, FI535, FI726 and mixtures thereof.

3. The method according to claim 1, wherein the conidia or formulation is applied to the structure such that the concentration of conidia on the surface of said structure is at least $10^8$ spores per $cm^2$.

4. The method according to claim 1, wherein said termites are of a genera selected from the group consisting of Coptotermes, Nasutitermes, Neotermes and Mastotermes.

5. A method of controlling termites in field applications comprising applying a prophylactic effective dose of conidia of a strain of *Metarhizium anisopliae* or formulations thereof, to the soil surrounding a structure to be protected from termite infestation.

6. The method according to claim 5, wherein the strain of *Metarhizium anisopliae* is selected from the group consisting of isolate FI610, FI535, FI726 and mixtures thereof.

7. The method according to claim 5 wherein the conidia applied to the soil such that the concentration of conidia is at least $10^8$ spores per gram of soil.

8. The method according to claim 5, wherein said termites are of a genera selected from the group consisting of Coptotermes, Nasutitermes, Neotermes and Mastotermes.

9. A method of controlling termites in field applications, comprising treating an infested area or structure with a curative dose of conidia of a strain of *Metarhizium anisopliae* or formulations thereof, such that the treatment will result in substantial termite colony mortality, said treating comprises distribution of said conidia or formulations substantially throughout said infested area or structure.

10. The method according to claim 9, wherein the strain of *Metarhizium anisopliae* is selected from the group consisting of isolate FI610, FI535, FI726 and mixtures thereof.

11. The method according to claim 9 or claim 10, wherein the conidia or formulations thereof are pumped or blown into the infested area or structure so as to ensure that the conidia or formulations thereof are substantially distributed throughout said area or structure.

12. The method according to claim 9, wherein said termites are of a genera selected from the group consisting of Coptotermes, Nasutitermes, Neotermes and Mastotermes.

13. A termite prophylactic formulation or a termite field curative formulation comprising a suspension of conidia of a strain of *Metarhizium anisopliae* in an aqueous solution of a water wetting agent.

14. A termite prophylactic formulation or a termite field curative formulation comprising conidia of a strain of *Metarhizium anisopliae* and an acceptable carrier, as a powder.

15. The formulation according to claim 13 or claim 14, wherein the formulation contains conidia in a concentration such that when the formulation is applied to a structure the concentration of conidia on the surface area to be treated is at least $10^8$ spores per cm$^2$.

16. The formulation according to claim 13 or claim 14, wherein the formulation contains conidia in a concentration such that when the formulation is applied to soil the concentration of conidia is at least $10^8$ spores per gram of soil.

17. The formulation according to claim 13 or claim 14, wherein the strain of *Metarhizium anisopliae* is selected from the group consisting of isolate FI610, FI535, FI726 and mixtures thereof.

18. A termite prophylactic formulation or a termite curative formulation comprising conidia of a strain of *Metarhizium anisopliae* and an acceptable carrier, as a bait.

19. The formulation according to claim 18, wherein the formulation contains conidia in a concentration in the bait within the range of $10^8$ to $10^9$ spores per gram.

20. The formulation according to claim 18 or claim 19, wherein the strain of *Metarhizium anisopliae* is selected from the group consisting of isolate FI610, FI535, FI726 and mixtures thereof.

21. The formulation according to claim 13 or claim 14, wherein the formulation contains conidia in a concentration such that when the formulation is applied to a structure the concentration of conidia on the surface area to be treated is at least $10^8$ spores per cm$^2$, and the strain of *Metarhizium anisopliae* is selected from the group consisting of isolate FI1610, FI535, FI726 and mixtures thereof.

22. The formulation according to claim 13 or claim 14, wherein the formulation contains conidia in a concentration such that when the formulation is applied to soil the concentration of conidia is at least $10^8$ spores per gram of soil, and the strain of *Metarhizium anisopliae* is selected from the group consisting of isolate FI610, FI535, FI726 and mixtures thereof.

* * * * *